United States Patent [19]
Ando et al.

[11] Patent Number: 5,370,634
[45] Date of Patent: Dec. 6, 1994

[54] DISPOSABLE DIAPER

[75] Inventors: Kenji Ando; Mitsue Ushiwata, both of Ichikai, Japan

[73] Assignee: Kao Corporation, Tokyo, Japan

[21] Appl. No.: 123,981

[22] Filed: Sep. 21, 1993

Related U.S. Application Data

[63] Continuation of Ser. No. 908,888, Jul. 7, 1992, abandoned, which is a continuation of Ser. No. 695,001, May 2, 1991, abandoned.

[30] Foreign Application Priority Data

May 9, 1990 [JP] Japan .................. 2-48216[U]
May 31, 1990 [JP] Japan .................. 2-142815

[51] Int. Cl.$^5$ .................. A61F 13/15; A61F 13/20
[52] U.S. Cl. .................. 604/385.1; 604/358; 604/385.2; 604/386; 604/389; 604/393; 604/394; 604/396; 604/400
[58] Field of Search .................. 604/358, 382–386, 604/389, 393–394, 396, 400, 402

[56] References Cited

U.S. PATENT DOCUMENTS

| | | | |
|---|---|---|---|
| 1,695,109 | 12/1928 | Kosloff | 604/396 |
| 2,055,973 | 9/1936 | Goss | 2/404 |
| 2,102,359 | 12/1937 | Frieman | 604/396 |
| 2,322,170 | 6/1943 | Snyder | 2/404 |
| 3,800,796 | 4/1974 | Jacob | 604/385.2 |
| 3,860,003 | 1/1975 | Buell | |
| 4,205,679 | 6/1980 | Repke et al. | 604/394 |
| 4,639,949 | 2/1987 | Ales et al. | |
| 4,850,988 | 7/1989 | Aledo et al. | 604/389 |
| 4,850,992 | 7/1989 | Amaral et al. | 604/389 |
| 4,940,464 | 7/1990 | Van Gompel et al. | 604/385.2 |
| 5,074,854 | 12/1991 | Davis | 604/385.2 |
| 5,236,430 | 8/1993 | Bridges | 604/385.1 |
| 5,246,433 | 9/1993 | Hasse et al. | 604/358 |

Primary Examiner—Jerome L. Kruter
Assistant Examiner—P. Zuttarelli
Attorney, Agent, or Firm—Birch, Stewart, Kolasch & Birch

[57] ABSTRACT

In an underpants type disposable diaper comprising a liquid permeable top sheet, a liquid impermeable back sheet, an absorbent member disposed therebetween, an elastic expansible member for forming a gather each to a pair of leg portions and front and rear waist body portions formed around the absorbent member, the front and rear waist body portions being connected and fixed together at both sides to form a waist opening portion and a pair of leg opening portions, respectively, at least a part of each area formed between the waist opening portions and the pair of leg opening portions at both side portions of the waist portion is provided with a vertical split portion, respectively and connection means are provided to each of the side portions.

19 Claims, 8 Drawing Sheets

DISPOSABLE DIAPER

This application is a continuation of application Ser. No. 07/908,888 filed on Jul. 7, 1992, now abandoned which is a continuation of application Ser. No. 07/695,001 filed on May 2, 1991, now abandoned.

BACKGROUND OF THE INVENTION

1. Field of the Invention

This invention relates to a disposable diaper for the use of infants, adults or incontinent persons.

2. Description of the Prior Art

Heretofore, many kinds of disposable diapers have been proposed. One typical disposable diaper is a so-called flat type which comprises a liquid permeable top sheet, a liquid impermeable back sheet, an absorbent member disposed therebetween, and a pair of side flaps, a pair of tape fasteners, disposed at both side edges of a waist portion on the back side of the side flaps, being fastened to the wearer's stomach side. Another example of such flat type disposable diaper is a disposable diaper 1 shown in FIG. 11. As is shown in FIG. 11, the disposable diaper 1 comprises, like the above-mentioned flat type disposable diaper, a top sheet 2, a back sheet 3, an absorbent member 4, and a pair of side flaps 15, 15, waist portions 15A, 15A in the back side of the side flaps 15, 15 being expanded sidewardly respectively, thereby forming a pair of expanded portions for covering the wearer's body portion, a pair of tape fasteners 16, 16 each provided to the corresponding expanded portions being fastened to an area-to-be-fastened 18 formed on a waist body portion 7 in the stomach side. Leg portions 15B and waist body portions 17 in the side flaps 15, 15 are provided with elastic members 19 and 110, respectively, in order to enhance fitness when the wearer wears the disposable diaper (Japanese Patent Publication No. Sho 52-40267).

Recently, a so-called underpants or drawers type disposable diaper was proposed, in which both side edges in the stomach side and back side of a pair of side flaps are attached and fixed together to form a pair of leg opening portions and a pair of waist opening portions, respectively (Japanese Patent Early Laid-open Publication No. Sho 61-207606). This drawers type disposable diaper is expansible at the leg and waist opening portions respectively so that it is intimately fitted to the wearer regardless of the wearer's figure. The wearer can usually wear such drawers type disposable diaper in the wearer's standing attitude. Therefore, this is very useful when used as toilet training, or for the-use of incontinent persons or adults who have difficulty in walking. Such drawers type disposable diaper also has an appearance of sewing finish which a good sewn product usually has and is intentionally made as a disposable underwear.

However, although the conventional drawers type disposable diaper has a flexible fitness to infants of high months age who moves actively, it has as a shortcoming that since the size of the waist opening portion is limited, it is difficult for the wearer to insert legs smoothly and the wear usually gives a feel of being narrow and tight. When the wearer flutters the feet, even more difficulty is encountered for wearing such drawers type disposable diaper. Moreover, the conventional drawers type disposable diaper has also a shortcoming that the wearer is always compel led to keep an awkward attitude when wearing whether the disposable diaper is for the use of infants or adults.

Furthermore, the conventional drawers type disposable diaper has as a shortcoming that it is not easy to tell whether there are waste materials discharged in the diaper while the wearer wears the diaper, which requires relying on the wearer's expression as an indication in order to make sure that the waste materials are already therein. Moreover, since no tape fastener is provided, it has another shortcoming that when the used disposable diaper is disposed, it is impossible to fasten the diaper using a tape fastener after waste materials are wrapped up within the diaper.

SUMMARY OF THE INVENTION

An object of the present invention is to provide a disposable diaper, in which the wearer is not compelled to keep an awkward attitude when wearing; the diaper can comparatively easily be put on even when the wearer is fluttering his or her feet; waste materials discharged in the diaper can easily be recognized from outside; and discharged waste materials can be wrapped up within the diaper for immediate disposal.

As a result of extensive study on the structure of a drawers type disposable diaper made by the inventors of the present invention, it was found that the above object can be achieved by providing a particular structure to connected portions at both sides of the front and rear waist body portions (wearer's stomach side and back side).

The present invention has been accomplished on a basis of the above-mentioned finding. According to the present invention, there is provided in a drawers type disposable diaper comprising a liquid permeable top sheet, a liquid impermeable back sheet, an absorbent member disposed therebetween, an elastic expansible member for forming a gather at each of a pair of leg portions and front and rear waist body portions formed around the absorbent member, said front and rear waist body portions being connected and fixed together at both sides to form a waist opening portion and a pair of leg opening portions, respectively, a disposable diaper being characterized in that at least a part of each area formed between said waist opening portions and said pair of leg opening portions at both side portions of said waist portion is provided with a vertical split portion, respectively and connection means are provided at each of said side portions.

According to the present invention, the diaper can be put on the wearer simply by fastening the connection means provided at both side portion of the waist portion after the wearer's feet are put into the pair of leg opening portions through the waist opening portion.

In the disposable diaper of the present invention, since at least a part of each area formed between the waist opening portions and the pair of leg opening portions at both side portions of the waist portion is provided with a vertical split portion, respectively, and connection means are provided at each of the side portions, the diaper can easily be put on the wearer without compelling the wearer to keep an awkward attitude when wearing and even when the wearer is fluttering his or her feet. Moreover, waste materials discharged in the diaper can easily be recognized from the outside and waste materials can be wrapped up within the diaper for immediate disposal.

The present invention also provides in a drawers type disposable diaper comprising a liquid permeable top sheet, a liquid impermeable back sheet, an absorbent member disposed therebetween, a pair of side flaps extending outwardly in the width direction of said absorbent member from each side edge in the longitudinal direction of said absorbent member, an elastic expansible member for forming a gather at each of the pair of side flaps, a disposable diaper being characterized in that at least a back side waist portion of each of the pair of side flaps is provided with a lateral split portion so that the waist portion is divided into at least two side flap elements, at least a pair of the side flap elements being connected and fixed to stomach side waist portions of the pair of side flaps to form a waist opening portion and a pair of leg opening portions, a pair of divided non-connected side flap elements being provided with a fastener means, respectively.

In the above-mentioned disposable diaper of the present invention, since at least a back side waist portion of each of the pair of side flaps is provided with a lateral split portion so that the waist portion is divided into at least two side flap elements, at least a pair of the side flap elements being connected and fixed to stomach side waist portions of the pair of side flaps to form a waist opening portion and a pair of leg opening portions, a pair of divided non-connected side flap elements being provided with a fastener means, respectively, the waist opening portion and the leg opening portions have sufficient room for inserting a wearer's legs, the wearer is not compelled to keep an awkward attitude when wearing and the disposable diaper can easily be put on the wearer even when the wearer is fluttering his or her legs. Moreover, according to the disposable diaper of the present invention, discharged waist materials contained in the disposable diaper can easily be recognized from the outside by peeling off the fastener means. Furthermore, since the connected and fixed side flaps can easily be torn in the vertical direction at the connected portions, the disposable diaper is not required to be pulled down to the wearer's feet when the disposable diaper is taken off. Therefore, there is no fear that the wearer's skin and clothing are dirtied by waste materials. Moreover, the disposable diaper containing waste materials discharged therein can be wrapped up with the diaper and fastened by the fastener means for immediate disposal.

DETAILED DESCRIPTION OF THE EMBODIMENT

The present invention will be described hereinafter with reference to FIGS. 1 through 5.

Figure 1:
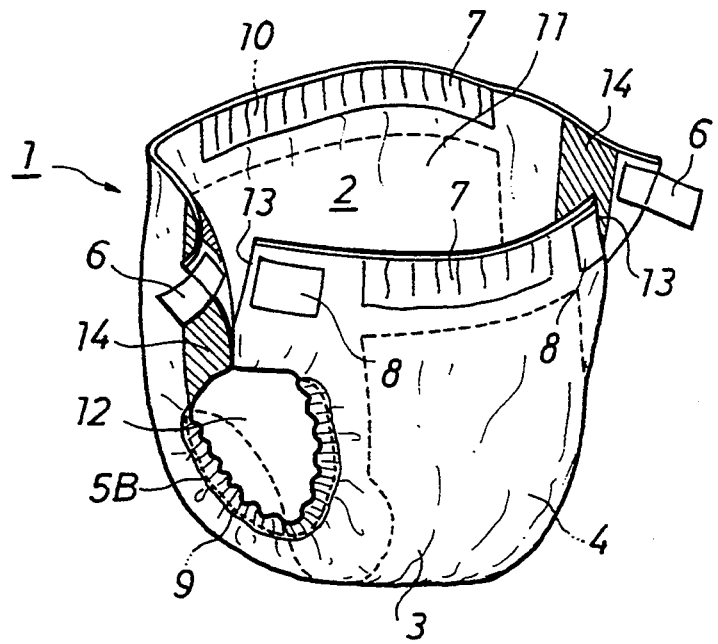
FIG. 1 is a perspective view showing one embodiment of a disposable diaper according to the present invention.
Figure 2:
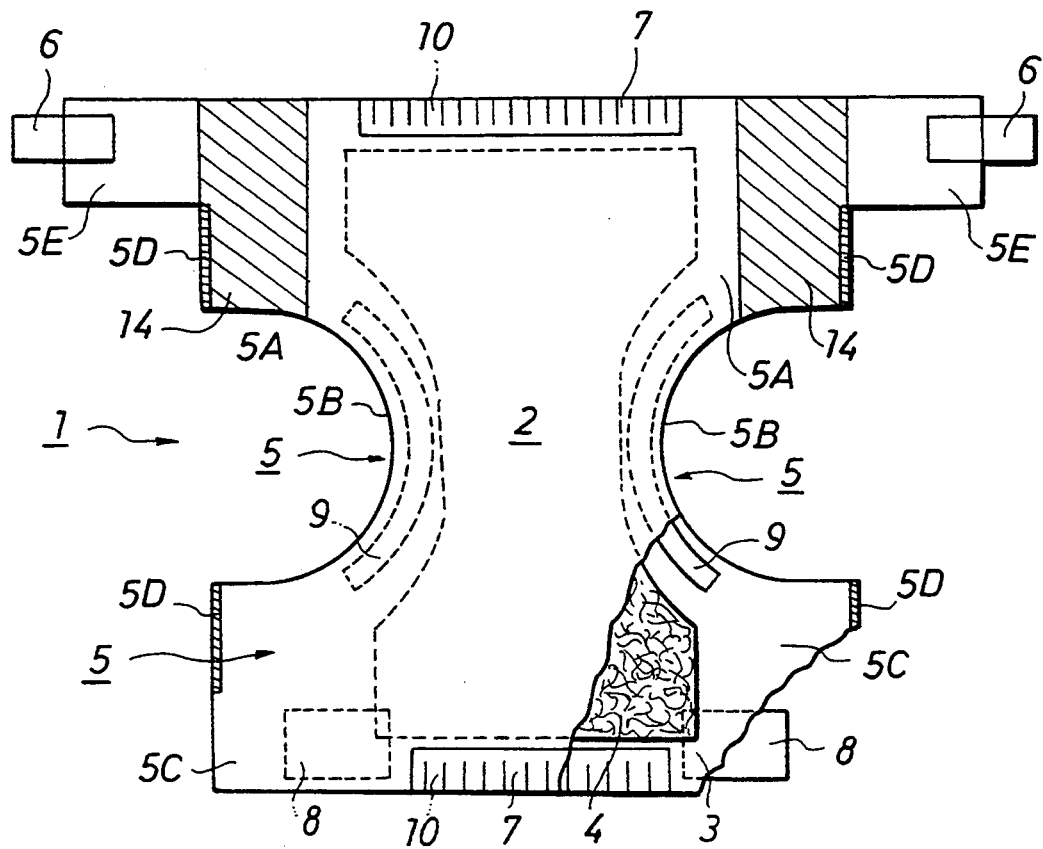
FIG. 2 is a plan view of an intermediate product, partly cut away, showing an outer surface side of the disposable diaper of FIG. 1 spread out.

A disposable diaper 1 of this embodiment is a drawers type disposable diaper and comprises, as shown in FIG. 1, a liquid permeable top sheet 2, a liquid impermeable back sheet 3, an absorbent member 4 disposed between the sheets 2 and 3, a pair of elastic expansible members 9 and 10 for forming a gather at each of a pair of side flap portions 5, 5 and of front and rear waist body portions 7, 7 formed outside the outer periphery of the absorbent member 4, the front and rear waist body portions 7, 7 being connected and fixed together at both sides to form a waist opening portion 11 and a pair of leg opening portions 12, 12, respectively. The side flaps 5, 5 are formed by extended portions of the top sheet 2 and back sheet 3 extending outwardly in the width direction from both side edge portions of the absorbent 4 and overlapped with each other. Leg portions 5B, 5B curved inwardly are formed at crotch areas of the side flaps 5, 5 as shown in FIG. 2.

At least a part of each area formed between the waist opening portions 11 and the pair of leg opening portions 12, 12 at both side portions of the waist portion is provided with a vertical split portion 13, respectively, (that is, each area starting from the upper edge of the waist opening portion 11 and ending at a mid-way to each leg opening portion 12 in this embodiment) and connection means (tape fasteners) 6 is provided for each split portion 13. The tape fasteners 6, 6 are formed on both sides of the rear waist body portion 7 separated by the split portions 13, 13 and are able to be fastened to viscous areas-to-be-fastened 8, 8 formed at both side portions of the front waist body portion 7. The tape fastener 6 is preferably a pressure sensitive adhesive tape, which has an adhesive sufficient enough not to be peeled off the area-to-be-fastened 8 when the wearer wears the diaper, the strength being at least 600 to 3000 g per inch in width, and more preferably, 1000 to 2000 g per inch in width.

The split portions 13, 13 will be further described with reference to an intermediate product of the spread-out disposable diaper 1 of FIG. 2. The split portions 13, 13 are formed at both sides of the front and Fear waist body portions 7, 7 as described above. More specifically, non-connected portions and connected portions 5D, 5D are continuously formed along the side edges of the respective waist portions 5A and 5C in the back side and stomach side of the side flaps 5, 5, the respective connected portions 5D, 5D are connected and fixed together, and the above-mentioned split portions 13, 13 are formed by the remaining respective non-connected portions. Furthermore, extending flaps 5E, 5E extending outwardly in the width direction are connected with the non-connected portions of the respective waist portions 5A, 5A in the back side, and the respective extending flaps 5E, 5E are provided with fasteners 6, 6. The connected portions 5D, 5D are inclined outwardly as it goes away from the leg portions 5B, 5B in FIG. 2. In the case where the waist opening portion 11 is formed, it is preferably formed such that the waist opening portion 11 is gradually expanded in the edge direction of the opening. The connected portion 5D is preferably 2 to 100 mm in length and more preferably 15 to 50 mm. The extending length of the extending flap 5E is preferably 5 to 100 mm, more preferably 20 to 70 mm and most preferably 25 to 50 mm. The tape fastener 6 is preferably equal in length to the extending length of the extending flap 5E and more preferably shorter than the extending length of the extending flap 5E.

Furthermore, elastic expansible members 14, 14 are arranged at the waist portions 5A, 5A in the back side of the respective side flaps 5, 5. It is preferably designed such that the elastic expansible members 14, 14 are expansible in the width direction about the wearer's body when the wearer wears the diaper.

The disposable diaper of this embodiment will be described in more detail. The absorbent member 4 is formed in a twisted hourglass shape at its under crotch area, and the top sheet 2 and back sheet 3 are also curved in conformity at under crotch areas thereof with the configuration of the absorbent member 4 as mentioned above. As is shown in FIG. 2, the elastic expansible members 9, 9 are stretched around the leg portions 5B, 5B of the respective side flaps 5, 5 and interposed between the sheets 2 and 3. Both the elastic expansible members 9, 9 are contracted in free states to form leg gathers shown in FIG. 1 in order to enhance fitness to the under crotch area. Two or more tape fasteners 6 may be provided to each of the extending flaps 5E, 5E.

The top sheet 2 used in the disposable diaper 1 of this embodiment is a liquid permeable sheet for permeating waste materials to the absorbent 4 and which preferably has a feel something like that of an underwear. Examples of such liquid permeable sheet are preferably woven fabrics, nonwoven fabrics, perforated films and the like. To prevent permeation leakage of waste materials such as urine and the like from the edge portion of the top sheet, a water repellent treatment may be applied to the edge portion of the top sheet by a method for applying a hydrophobic compound such as silicon series oil solution, paraffin wax and the like to the edge of the top sheet or by a method for applying a hydrophilic compound such as alkyl phospholic ester to the edge of the top sheet in advance and then cleaning the edge with hot water.

The back sheet 3 used in the disposable diaper 1 is preferably a moisture permeable and liquid impermeable sheet able to permeate vapor therethrough and formed of a thermoplastic resin and filler added thereto and stretched and more preferably a sheet having a feel something like that of an underwear. Examples of such liquid impermeable sheet are preferably a composite material of film and woven fabric or a composite material of film and non-woven fabric.

The absorbent member 4 used in the disposable diaper 1 of this embodiment is preferably comprised of an open cell pulp as a chief component material and a high molecular water absorbent polymer as a secondary material, or a mixture of a thermoplastic resin, a cellulosic fiber and a high molecular water absorbent polymer subjected to heat treatment. The existing position of the high molecular water absorbent polymer may be in an upper layer, an intermediate layer or a lower layer, and the high molecular water absorbent polymer may be mixed with pulp. The high molecular water absorbent polymer preferably has an ability for absorbing and holding liquid more than twenty times the dead weight thereof and is in a grain shape having a property able to be gel led. Examples of such high molecular water absorbent polymer are preferably starch-acrylic (salt) graft copolymer, a saponified material of starch-acrylonitrile copolymer, bridged material of sodium carboximethylcellulose, acrylic (salt) polymer and the like.

The elastic expansible materials 9 and 10 used in the disposable diaper of this embodiment are preferably yarn rub bets, flat rubbers, film type rubbers, and preferably 70 to 100 g when stretched 100%. The elastic expansible member 14 is preferably of non-woven fabric type having expansibility and breathability.

Figure 3:
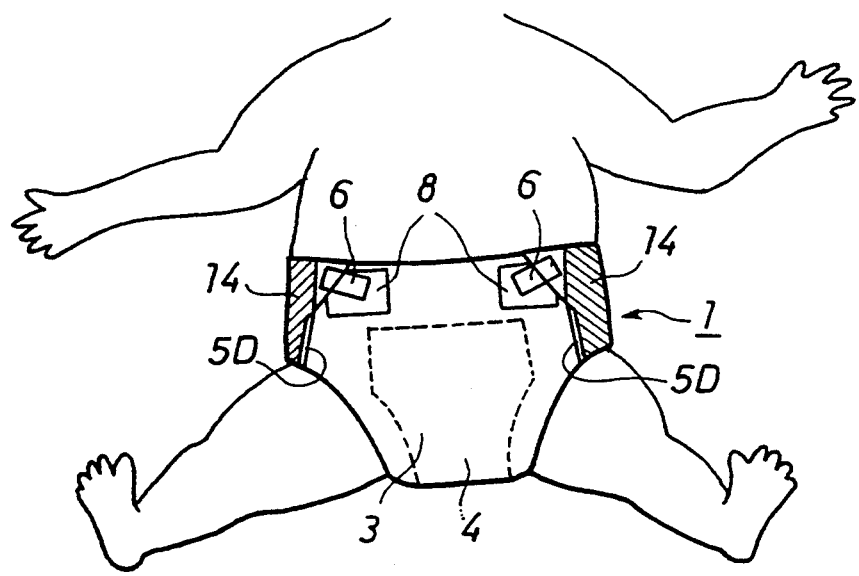
FIG. 3 is a perspective view showing the disposable diaper of FIG. 1 which is already put on an infant.

Since the disposable diaper 1 of this embodiment has the above-mentioned constitution, when the diaper is to be put on, for example, an infant, the waist opening portion 11, as shown in FIG. 3, is spread at the split portions 13, 13 first and then the waist opening portion 11 is further stretched by stretching the elastic expansible members 14, 14. After both legs of the infant are inserted into the pair of leg opening portions 12, 12, the split portions 13, 13 at both sides of the waist body portions 7, 7 are pulled nearer and the extending portions 5E, 5E are overlapped at the waist body portion 7 on the stomach side of the infant. Then, the tape fasteners 6, 6 are fastened to the areas-to-be-fastened 8, 8.

Therefore, according to the disposable diaper 1 of this embodiment, since the disposable diaper 1 can be put on the wearer simply by connecting the split portions 13, 13 through the tape fasteners 6, 6 after the pair of legs are inserted into the pair of leg opening portions 12, 12 through the waist opening portion 11 loosened by the split portions 13, 13 at the upper edge, the diaper can easily be put on the wearer without compelling the wearer to keep an awkward attitude. Even when the wearer is moving actively in such a manner as to flutter the legs hard, the diaper can easily be put on the wearer simply by inserting the legs through the widely spread waist opening portion 11. Also, in the disposable diaper 1 of this embodiment, the inside can easily be recognized simply by unfastening the tape fasteners 6, 6 from the areas-to-be-fastened 8, 8. Furthermore, the disposable diaper 1 already containing waist materials discharged by the wearer can simply be wrapped up within the diaper and fastened by the tape fasteners 6, 6 for immediate disposal.

Figure 4:
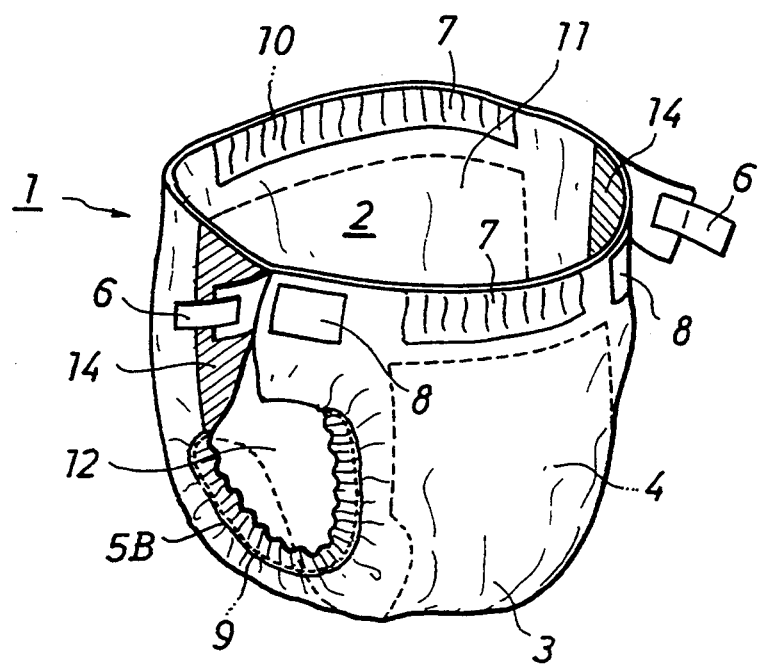
FIG. 4 is a perspective view corresponding to FIG. 1 but showing another embodiment of a disposable diaper according to the present invention.
Figure 5:
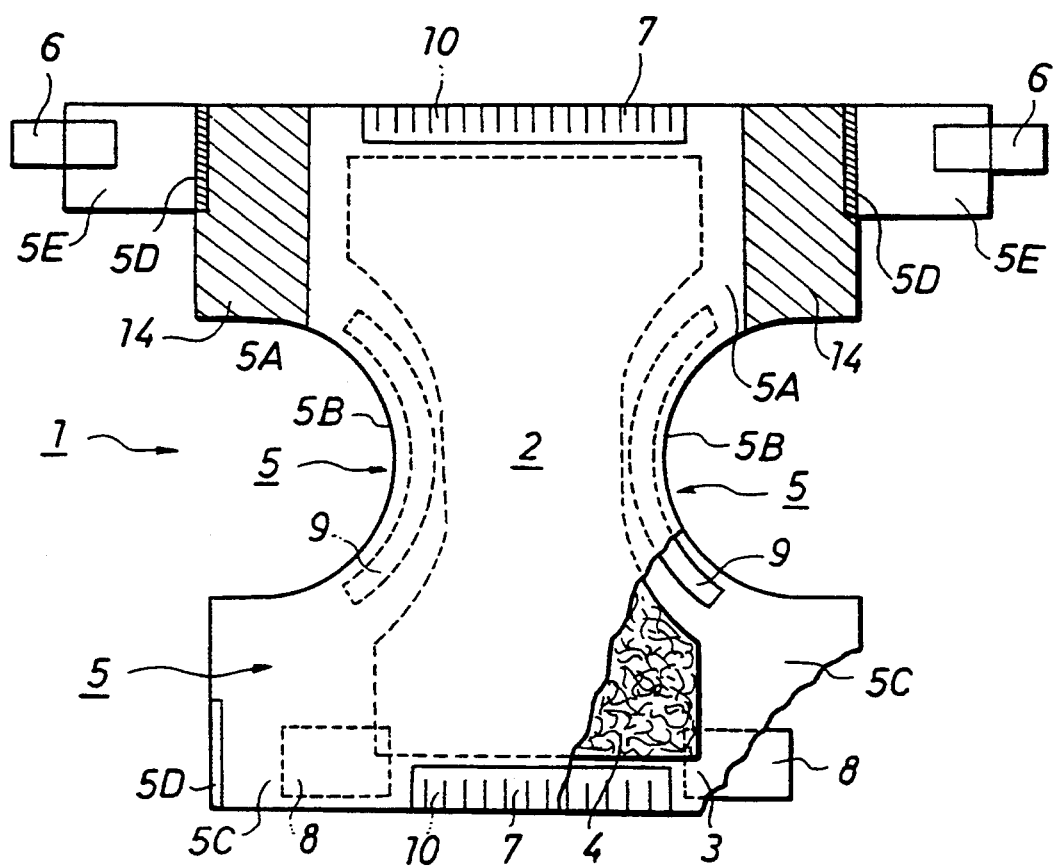
FIG. 5 is a perspective view corresponding to FIG. 2 of the disposable diaper of FIG. 4.

FIGS. 4 and 5 show another embodiment of the present invention. The disposable diaper 1 of this embodiment is constituted in the same way as the preceding embodiment except that a pair of vertical split positions 13, 13 are respectively formed at both side portions of the waist body portions 7, 7, starting from a pair of leg openings 12, 12 toward the waist opening portion 11 and ending at mid-way to the waist opening portion 11 and the leg opening portion 12, and a pair of tape fasteners 6, 6 are arranged in such a manner as to be one-sided toward the waist opening portion 11 as shown in FIG. 4 and 5. Therefore, according to the disposable diaper 1 of this embodiment, since the leg opening portions 12, 12 are loosened, it has such advantages as that the legs of the wearer can easily be inserted into the leg opening portions 12, 12, and the wearer can be free from a feel of tightness when the wearer wears the diaper, besides the advantages already mentioned above in connection with the preceding embodiment.

It is noted that the positions of the split portions and the connection means are not limited to the above-mentioned embodiment as long as vertical split portions are formed in at least a part of each area between the waist opening portion and a pair of leg opening portions at both side portions of the waist portion, connection means are formed at both side portions thereof, respectively, and elastic expansible members are arranged at both side portions thereof, respectively.

Next, the present invention will be described with reference to FIGS. 6 through 10.

The expression "side flap(s)" used in this specification refers to the extending portion(s) extending outwardly in the width direction of the absorbent member from both side edges in the longitudinal direction of the absorbent member, the expression "waist body portion" refers to a portion around the waist portion (the portion denoted by the numerals 7 17 in the drawings), and the expression "waist portion(s)" refers to a waist portion(s) of the side flap(s), i.e., the flaps on both side edges of the back side or stomach side waist body portion.

Figure 6:
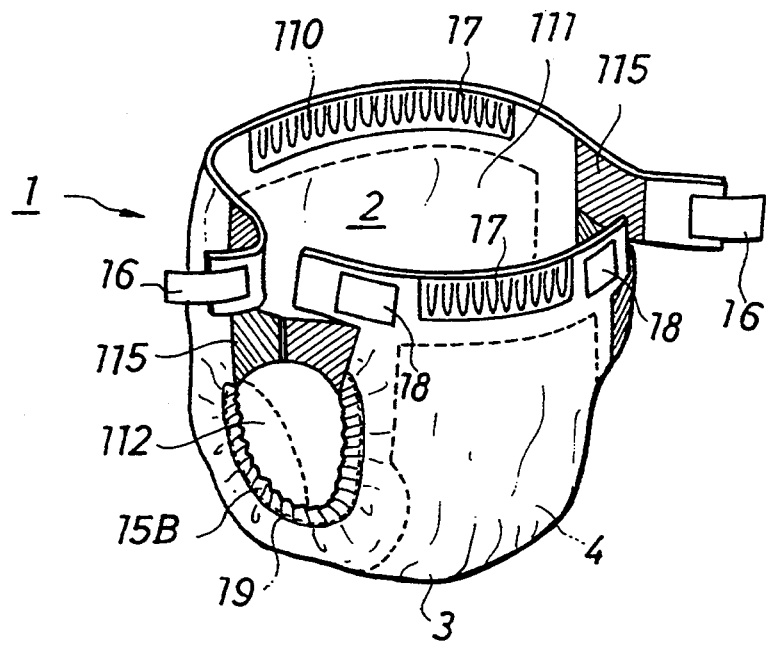
FIG. 6 is a perspective view showing still another embodiment of a disposable diaper according to the present invention.

The disposable diaper 1 of this embodiment comprises, as shown in FIG. 6, a liquid permeable top sheet 2 forming the side contacting the wearer's skin, a liquid impermeable back sheet 3 corresponding to the top sheet 2, an absorbent member 4 disposed and fixed between the sheets 2 and 3 and adapted to absorb waste materials, a pair of side flaps 15, 15 extending outwardly in the width direction from both side edges of the back side first edge and of the stomach side second edge in the longitudinal direction of the absorbent member 4, and a pair of elastic expansible members 19, 19 for forming gathers to the leg portions 15B, 15B of the pair of side flaps 15, 15, the back side waist body portion 17 and the stomach side waist body portion 17', as will be described afterward, being partly connected and fixed at both ends thereof to form a waist opening portion 111 and a pair of leg opening portions 112, 112, respectively. The side flaps 15, 15 are formed by the top sheet 2 and back sheet 3 extending outwardly in the width direction from both side edges of the absorbent member 4 and overlapped with each other, and a pair of leg portions 15B, 15B curved inwardly as shown in the drawings are formed in the under crotch areas of the side flaps 15, 15.

Figure 7:
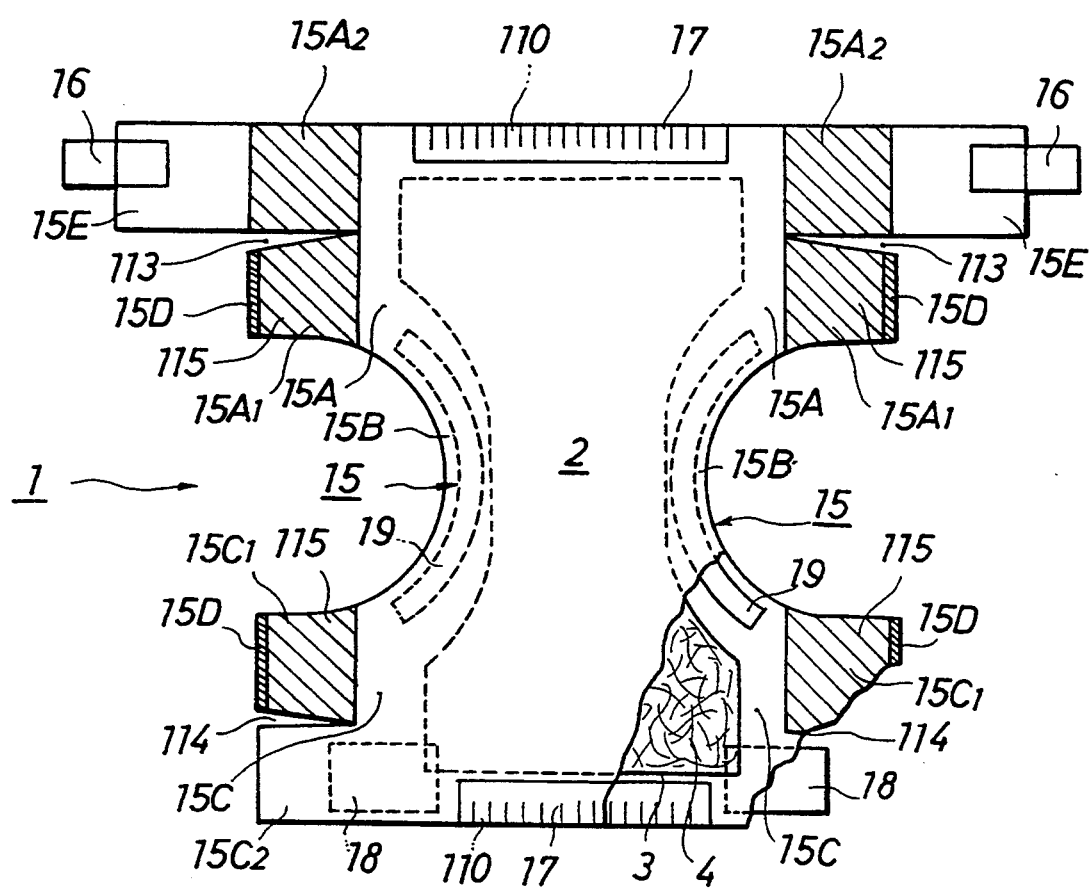
FIG. 7 is a plan view of an intermediate product, partly cut away, showing an outer surface side of the disposable diaper of FIG. 6 spread out.

In the disposable diaper 1 of this embodiment, as is shown in a spread-out state in FIG. 7, the back side waist portions 15A, 15A of the above-mentioned pair of side flaps 15, 15 are provided with lateral split portions 113, 113, respectively, so that the waist portions 15A, 15A in the pair of side flaps 15, 15 are divided into two side flap elements 15A$_1$, 15A$_2$, respectively. On the other hand, the stomach side waist portions 15C, 15C of the above-mentioned pair of side flaps 15, 15 are also provided with similar lateral split portions 114, 114, so that the pair of side flaps 15C, 15C are divided into two side flap elements 15C$_1$, 15C$_2$, respectively. The back side opposed side flap elements 15A$_1$, 15A$_1$ and the stomach side opposed side flap elements 15C$_1$, 15C$_1$, which are located on the side of the leg portions 15B, 15B, are connected to each other at the respective connected portions 15D, 15D to form a waist opening portion 111 and a pair of leg opening portions 112, 112 (see FIG. 6).

Furthermore, it is preferable in view of function that elastic expansible members 115, 115 are disposed on the entirety of the respective side flap elements 15A$_1$, 15A$_2$, and elasticity is provided to the respective side flap elements 15A$_1$, 15A$_2$ so that the respective side flap elements 15A$_1$, 15A$_2$ can be independently expanded and contracted, the elastic expansible members 115, 115 being expanded or constructed in the width direction when the wearer wears the disposable diaper. Also, as the connected and fixed side flaps 15A$_1$, 15C$_1$ are preferably designed such as to be able to be torn in the vertical direction, so that the skin of the wearer is not dirtied, the disposable diaper can easily be torn at the connected portions 15D, 15D, and the disposable diaper 1 can easily be taken off and disposed of. The elastic expansible member 115 is preferably provided to the entire length in the extending direction of the side flaps 15A$_1$, 15A$_2$ and to at least a part thereof in the width direction.

Furthermore, it is preferable that the connected portions 15D, 15D use a raw material able to be connected by, for example, hot melt adhesive or ultrasonic welding and these portions 15D, 15D are soft in touch even after being connected (welded). The length of each of the connected portions 15D, 15D is preferably 2 to 100 mm and more preferably 15 to 50 mm.

Furthermore, the flaps 15E, 15E extending outwardly in the width direction are connected with the side edges of the pair of back side non-connected side flap elements 15A$_2$, 15A$_2$, the respective extending flaps 15E, 15E are provided with fastener means (tape fasteners) 16, 16, and the tape fasteners 16, 16 are fastened to the areas-to-be-fastened 18, 18 formed on both side edges of the stomach side waist body portion 17 to have the wearer wear the disposable diaper. The length of the tape fastener 16 is preferable equal to or shorter in viscous surface than the extending length of the extending flap 15E. The tape fastener 16 is preferably a pressure sensitive adhesive tape, the tape fastener 16 preferably has strength enough not to be peeled off the area-to-be-fastened 18 when the wearer wears the disposable diaper and the strength is preferably at least 600 to 3000 g and more preferably 1000 to 2000 g per inch in width when it is pulled in the horizontal direction in plane. Also, the tape fastener 16 preferably has expansibility. By using a tape fastener 16 having such expansibility, the disposable diaper 1 can easily put on the wearer and the fastening force of the tape fastener 16 can be adjusted. The raw material of the tape having such expansibility is preferably an elastic member expansible 30 to 400% with a tensile force of 1000 to 1500 g/cm, and in order to obtain effective fitness to the waist portion of the wearer, the permanent distortion of the elastic member, when expanded 100%, is preferably 30% or less. The extending length of the extending flap 15E is preferably 5 to 100 mm and more preferably 25 to 50 mm.

Furthermore, the disposable diaper 1 of this embodiment is formed at an under crotch area thereof in a twisted hourglass shape, and the top sheet 2 and back sheet 3 are also curved in the under crotch area in conformity with the configuration of the absorbent member 4 as mentioned above. The side flaps 15, 15 are provided at the leg portions 15B, 15B with elastic expansible members 19, 19 stretched between the sheets 2 and 3 in the curved states as shown in FIG. 7. These elastic expansible members 19, 19 are contracted in the free states to form leg gathers so as to be well fitted to the under crotch area as shown in FIG. 6. Two or more tape fasteners 16 may be provided to each of the extending flaps 15E, 15E, respectively.

The component materials of a diaper such as top sheet 2, back sheet 3, absorbent member 4, elastic member and the like which are used in this embodiment and in the embodiment(s) to be described hereinafter are the same used in the corresponding parts of the embodiment shown in FIG. 2. The elastic expansible member 115 is preferably of non-woven fabric type having expansibility and breathability.

Figure 8:
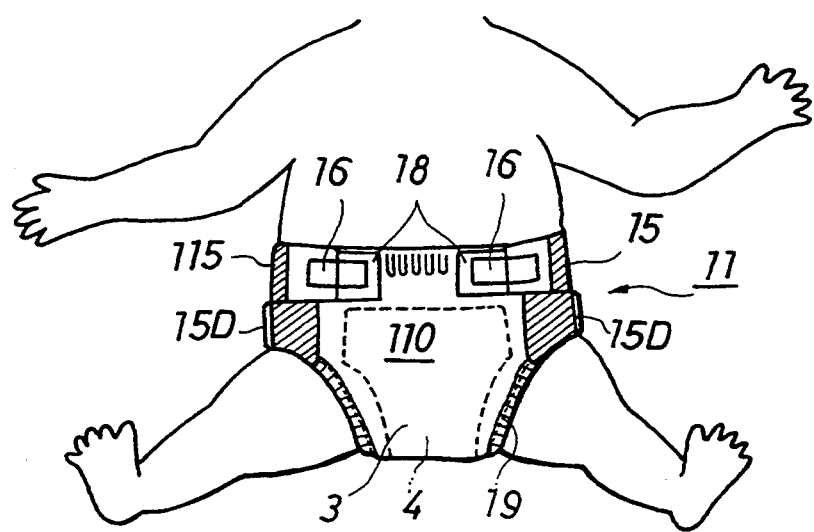
FIG. 8 is a perspective view of the disposable diaper of FIG. 6 which is already put on an infant.

Since the disposable diaper 1 of this embodiment has above-mentioned construction, as shown in FIG. 8, the tape fasteners 16, 16, when wearing, are spread sidewardly to widen the a waist opening portion 111 first, then the elastic expansible member 115 is expanded in the connected side flaps $15A_1$, $15C_1$ and the legs of the infant are inserted into leg opening portions 112, 112, and thereafter non-connected extending flaps 15E, 15E at both side portions of the waist portions 17, 17 are pulled nearer to overlap the extending flaps 15E, 15E at stomach side side flap elements $15C_2$, $15C_2$, and then the tape fasteners 16, 16 are fastened to the areas-to-be-fastened 18, 18.

Therefore, according to the disposable diaper 1 of this embodiment, simply by fastening the tape fasteners 16, 16 to the stomach side areas-to-be-fastened 18, 18 after the wearer's legs are inserted into the leg opening portions 112, 112 through the waist opening portion 111 loosened at an upper end thereof by two pairs of non-connected side flap elements $15A_2$, $15C_2$, the disposable diaper 1 of this embodiment can be put on the wearer. Since the waist opening portion 111 and the leg opening portions 112, 112 are wide and these opening portions 111, 112 have sufficient room at a stage before the tape fasteners 16, 16 are fastened, the disposable diaper 1 can easily be put on the wearer without compelling the wearer to keep an awkward attitude. Also, even when the wearer is moving actively in such a manner at to flutter the legs hard, the disposable diaper can easily be put on the wearer simply by inserting the legs through the widened waist opening portion 111, and after the disposable diaper is put on the wearer, the entire periphery of the leg portion starting from elastic expansible members 19, 19 forming the entire periphery of the leg portions 15B, 15B and ending at the side flap elements $15A_1$, $15A_1$ exhibits independent expansibility from the entire periphery of the waist portions starting from the tape fasteners 16, 16 and ending at the waist flap via the side flap elements $15A_2$, $15A_2$, thereby ensuring sealing performance at the leg portions. It is noted that a disposable diaper in which the entirety of the diaper or a part thereof starting from the waist opening portions at both sides and ending at the leg opening portions are formed of a same elastic expansible member is already commercially available. However, since such type of a disposable diaper is integral in the elastic expansible member from the waist opening portion to the leg opening portions, the expanding and contracting force of the leg portions caused by movement of the legs such as walking is transmitted to the waist portions to enhance slipping-off of the disposable diaper or otherwise, the dimension about the waist portions is changed owing to change in the wearer's attitude and this change is transmitted to the leg portions to enhance slipping-off of the disposable diaper. In the disposable diaper 1 of this embodiment, however, since expanding forces of the waist portions and leg portions function independently, it does not have the above-mentioned inconvenience. Moreover, by using different raw materials having different expanding forces to the respective elastic expansible members 115, 115 for the side flap element $15A_1$ on the leg opening portion side and for the side flap element $15A_2$ on the waist opening portion side, fitness of the disposable diaper 1 can be obtained in its best mode.

Furthermore, in the disposable diaper 1 of this embodiment, since the inside of the disposable diaper 1 can easily be recognized from outside by unfastening the tape fasteners 16, 16 from the areas-to-be-fastened 18, 18 and the connected and fixed side flaps $15A_1$, $15C_1$ can easily be torn in the vertical direction, the disposable diaper 1 is not required to be pulled down to the feet when the disposable diaper 1 is taken off. As a result, there is no fear that the wearer's clothing is dirtied with waste materials discharged. Also, the disposable diaper 1 containing waste materials already discharged therein can be wrapped up with the diaper and fastened with the tape fasteners for immediate disposal.

Figure 9:
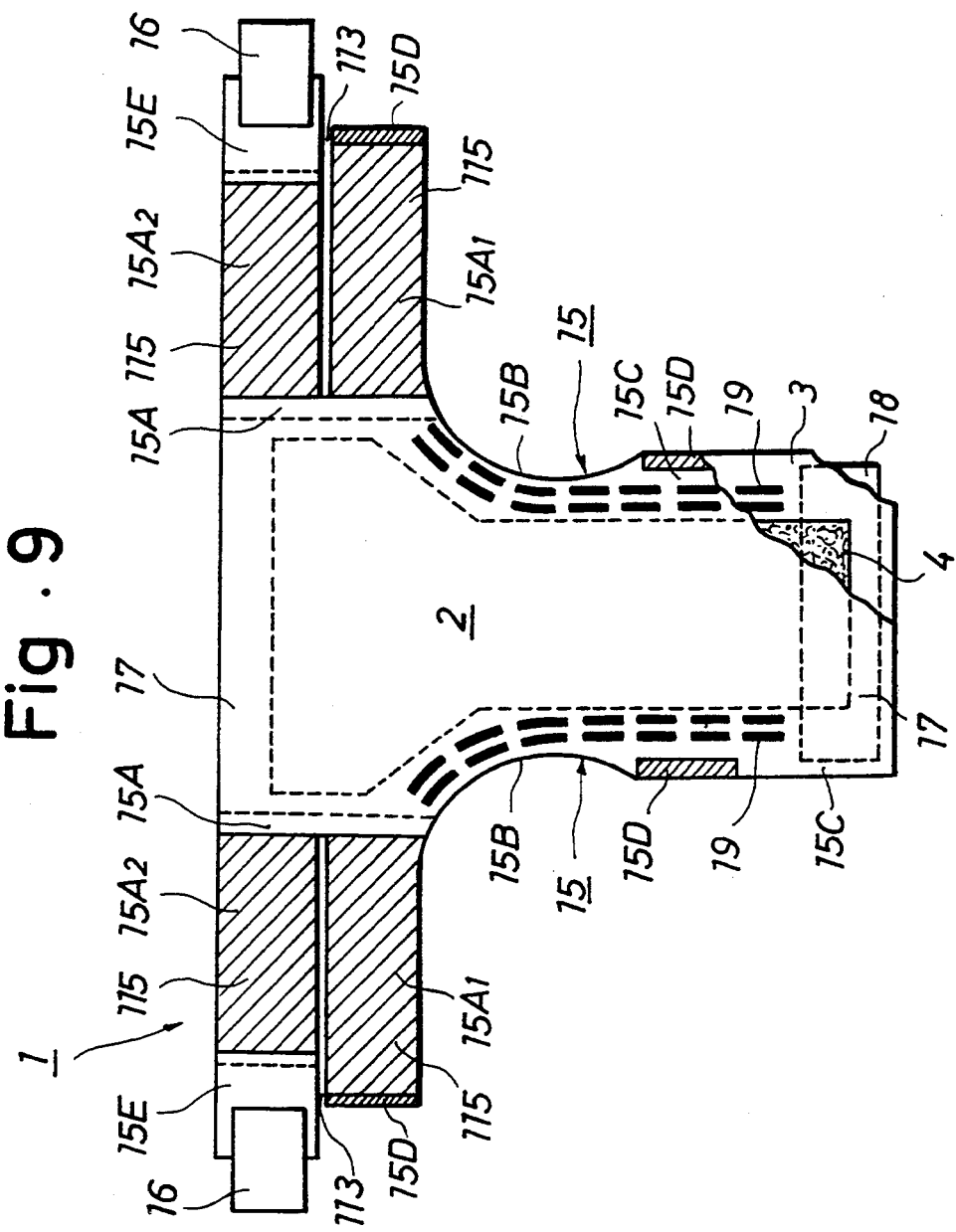
FIGS. 9 and 10 are plan views corresponding to FIG. 7 but showing still another embodiment of a disposable diaper according to the present invention.

FIG. 9 is a view showing another embodiment of the present invention. In the disposable diaper 1 of this embodiment, the side flap elements $15A_1$, $15A_2$ on the back side are longer in the width direction than those of the above-mentioned embodiment, while the side flaps 15C, 15C on the stomach side integrally extend less without forming split portions in the width direction from both side edges of the absorbent member 4. That is, the total length of the length in the width direction of the side flap element $15A_1$ on the back side and the length in the width direction of the side flap 15C on the stomach side is approximately equal to the total length of the length in the width direction of the side flap element $15A_1$ on the back side in the above-mentioned embodiment and the length in the width direction of the side flap element 15C on the stomach side therein. And the side flap elements $15A_1$, $15A_1$ on the side of the leg portions 15B, 15B are connected with the narrow side flaps 15C, 15C on the stomach side, respectively. The elastic expansible members 115, 115 for providing expansibility to the respective side flap elements $15A_1$, $15A_2$ are preferably formed over the entire length in the extending direction thereof and in at least a part in the width direction thereof. The width is preferably 5 to 150 mm and more preferably 30 to 80 mm. The absorbent member 4 is formed wide in a hip portion thereof and the remaining portion thereof has the same width. Two strip-like elastic expansible members 19 are disposed along both side edges of the absorbent member 4, respectively. An area-to-be-fastened 18 is formed over the entirety of the stomach side waist body portion 17. The disposable diaper 1 of this embodiment may also be designed such that the side flaps 15C, 15C on the stomach side are omitted and the side flap element $15A_1$ on the back side is directly attached to the back sheet 3 and/or top sheet 2 located at the side edges of the absorbent member 4. Accordingly, the disposable diaper 1 of this embodiment exhibits the similar function and effect as in the disposable diaper 1 of the above-mentioned embodiment.

Figure 10:
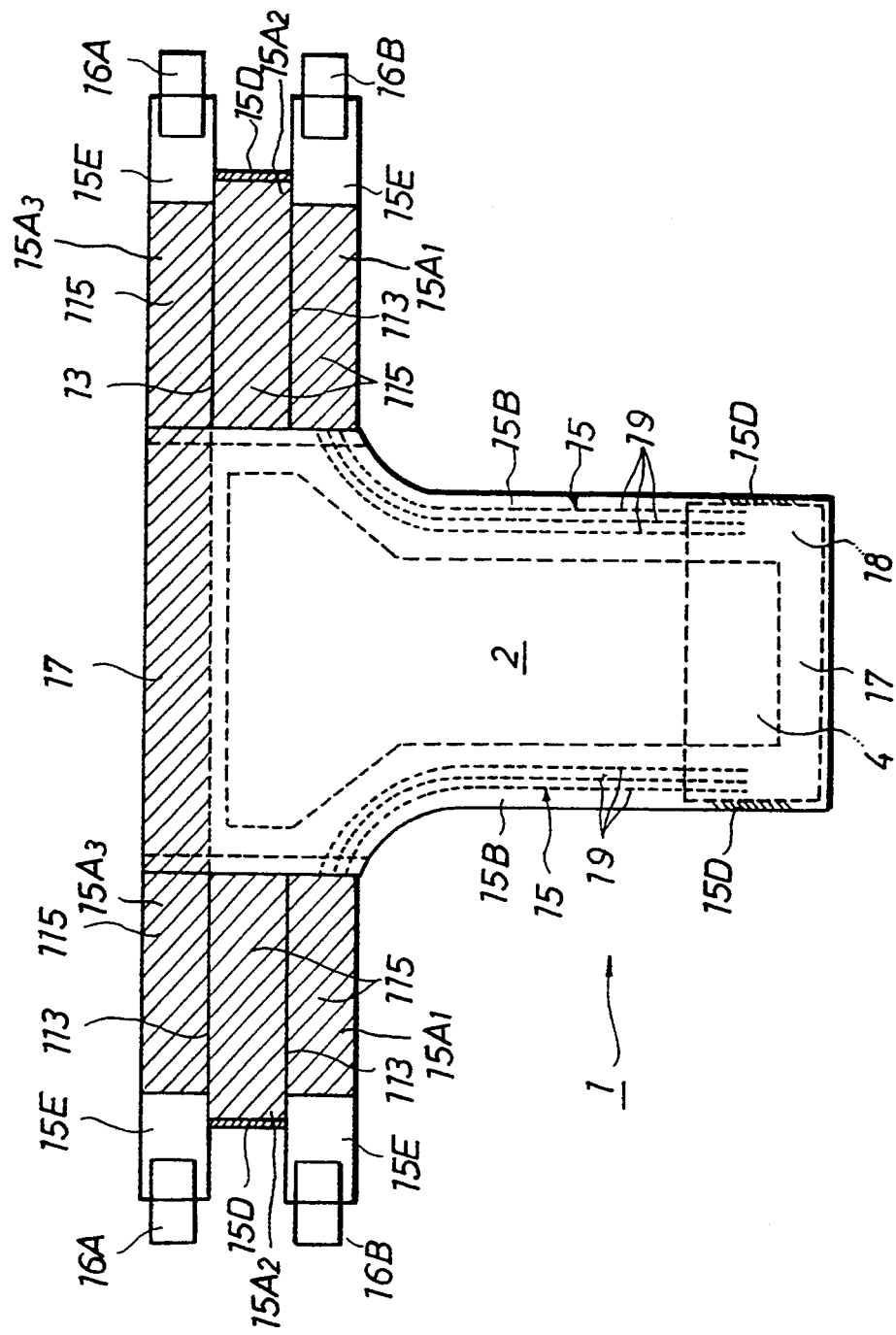
Figure 11:
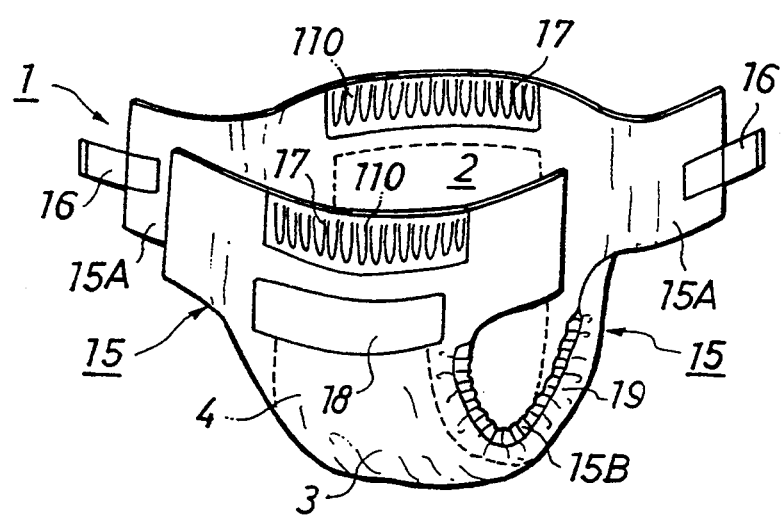
FIG. 11 is a perspective view showing one embodiment of a conventional flat type disposable diaper.

FIG. 10 shows still another embodiment of a disposable diaper of the present invention. In the disposable diaper 1 of this embodiment, the side flap 15A on the back side is divided into three portions. The extending flaps 15E, 15E of the side flap elements $15A_1$, $15A_3$ on the side of the leg opening portion 112 and on the side of the waist opening portion 111 are provided with tape fasteners 16A, 16B, respectively. The connected portion 15D of the central side flap element $15A_2$ is connected and fixed to the connected portion 15D on the stomach side of the waist portion. Each of the side flap elements $15A_1$, $15A_2$ and $15A_3$ is formed of elastic expansible member having breathability. Particularly, the side flap element $15A_3$ on the side of the waist opening portion 111 is formed by extending an elastic expansible member of a waist gather. All the remaining parts are constructed in the same manner as the above-mentioned embodiments. Accordingly, the disposable diaper 1 of this embodiment also exhibit the similar function and effect as in the disposable diaper 1 of the above-mentioned embodiments. In addition, since two pairs of tape fasteners are provided to the disposable diaper 1 of this embodiment, the fastening portion is long and thus suitable when used for adults and incontinent persons.

The disposable diaper 1 of this embodiment suffices if at least the waist portions on the back side of the pair of side flaps are provided with split portions in the width direction, respectively so that the waist portions are divided into at least two side flap elements, at least a pair of side flap elements being connected and fixed to the waist portion on the stomach side to form a waist opening portion and a pair of leg opening portions, the non-connected side flap elements being provided with faster means respectively. Particularly, for the use of infants, the side flap elements located on the leg portion side are preferably connected, and for the use of adults, the side flaps are preferably divided into three parts and two pairs of tape fasteners are provided thereto because such designed disposable diaper properly fits to the length of the wearer's body and a favorable feel of fitness is available. It is noted, however, that the number of split portions, the number of fastener means, the length of the side flap elements, etc. are not limited to the above-mentioned embodiments as long as they do not jeopardize the function of the disposable diaper.

What is claimed is:

1. An underpants type disposable diaper comprising an integrated sheet, said integrated sheet including a liquid permeable top sheet, a liquid impermeable back sheet, and an absorbent member having a periphery, said absorbent member being disposed between said top sheet and said back sheet, said integrated sheet having a front waist body portion and a rear waist body portion and first and second side portions, each of said side portions having a concave section, said front waist body portion and said rear waist body portion each having a first waist flap and a second waist flap, each of said first waist flaps and said second waist flaps having a first portion and a second portion, each said first portion of said first waist flaps being fixedly interjoined by a manually tearable pre-connected portion to form a first joint and each said first portion of said second waist flaps being fixedly interjoined by a manually tearable pre-connected portion to form a second joint such that a pair of leg opening portions and a waist opening portion are formed, each of said first and second joints being separable by tearing along a longitudinal axis thereof, respectively, a plurality of elastic expansible members for forming a gather adjacent to the periphery of said absorbent member at each of said leg opening portions, one of each said second portion of said first and second waist flaps containing first and second connection means, respectively, for removably connecting each of said first waist flaps together and each of said second waist flaps together, respectively.

2. The disposable diaper as claimed in claim 1, wherein said plurality of elastic expansible members include a pair of leg opening elastic expansible members, one of said pair of leg opening elastic expansible members being disposed adjacent each said concave section.

3. The disposable diaper as claimed in claim 1, wherein said first and second connection means are disposed adjacent said waist opening portion on said second portions of said first waist flaps and said second portions of said second waist flaps, respectively.

4. The disposable diaper as claimed in claim 1, wherein each of said first portions of said first waist flaps and of said second waist flaps are adjacent to one of said pair of leg opening portions, respectively.

5. The disposable diaper as claimed in claim 1, wherein each of said first portions of said first waist flaps and of said second waist flaps are adjacent to said waist opening portion.

6. A disposable diaper comprising an integrated sheet, said integrated sheet including a liquid permeable top sheet, a liquid impermeable back sheet, and an absorbent member, said absorbent member being disposed between said top sheet and said back sheet, said integrated sheet having a front waist body portion, a rear waist body portion and first and second side portions, each of said side portions having a concave section, said front waist body portion having a first front waist flap and a second front waist flap, and said rear waist body portion having a first rear waist flap and a second rear waist flap, each of said waist flaps being split apart into a first element and a second element, said second elements of said first front waist flap and of said first rear waist flap being interjoined by a manually tearable pre-connected portion to form a first joint and said second elements of said second front waist flap and of said second rear waist flap being interjoined by a manually tearable pre-connected portion to form a second joint such that a pair of leg opening portions and a waist opening portion are formed, each of said first and second joints being separable by tearing along a longitudinal axis thereof, respectively, and first and second fastener means for removably fastening said first elements of said first front waist flap and said first rear waist flap together, and said first elements of said second front waist flap and said second rear waist flap together, respectively.

7. The disposable diaper as claimed in claim 6, wherein each said first element includes an expansible portion.

8. The disposable diaper as claimed in claim 6, wherein each of said first and second elements include an expansible portion.

9. The disposable diaper as claimed in claim 6, wherein each of said fastener means includes an expansible portion.

10. The disposable diaper as claimed in claim 6, wherein each of said first front waist flap, said second front waist flap, said first rear waist flap and said second rear waist flap includes an elastic expansible member adapted to form a gather.

11. A pull-on type disposable diaper comprising:
an integrated sheet including a liquid permeable top sheet, a liquid impermeable back sheet, and an absorbent member disposed between said top sheet and said back sheet;
a front waist body portion, a rear waist body portion, and first and second side portions provided on said integrated sheet, each of said side portions having a concave section defining leg openings of said diaper;
a first longitudinally manually tearable pre-connected portion connecting each of said side portions of said integrated sheet together; and
a second selectively fastenable portion at each of said side portions of said integrated sheet;

wherein said pull-on type disposable diaper is applied to a wearer in a pull on manner followed by fastening of said second selectively fastenable portion and removed from a wearer by releasing said second selectively fastenable portion and longitudinally tearing said pre-connected portion.

12. The pull-on type disposable diaper as claimed in claim 11, wherein said leg openings include a pair of leg opening elastic expansible members, one of said pair of leg opening elastic expansible members being disposed adjacent each said concave section.

13. The pull-on type disposable diaper as claimed in claim 11, wherein each of said front waist body portion and said rear waist body portion include an elastic expansible member adapted to form a gather.

14. The pull-on type disposable diaper as claimed in claim 11, wherein said tearable preconnected portion is positioned adjacent an upper edge of said pull-on diaper and coextensively with said second selectively fastenable portion.

15. The pull-on type disposable diaper as claimed in claim 11, further including a slit portion formed at each of said first and second side portions from said leg openings to a height not greater than an upper edge of each of said first and second side portions.

16. The pull-on type disposable diaper as claimed in claim 11, wherein said first longitudinally tearable preconnected portions are laterally split from said second selectively fastenable portions.

17. The pull-on type disposable diaper as claimed in claim 11, wherein said first and second side portions are formed of an elastically expansible material.

18. The pull-on type disposable diaper as claimed in claim 11, wherein said tearable preconnected portion extends at least one-half a height of the side portion of the integrated sheet.

19. The pull-in type disposable diaper as claimed in claim 18, wherein said selectively fastenable portion is positioned above said tearable preconnected portion.

* * * * *